United States Patent
Choi et al.

(10) Patent No.: US 7,803,540 B2
(45) Date of Patent: Sep. 28, 2010

(54) METHOD OF INCREASING DISCRIMINATION FOR SINGLE BASE MISMATCH USING HURDLE DNA AND ARTIFICIALLY MISMATCHED PROBE

(75) Inventors: Soo-hyung Choi, Hwaseong-si (KR); Jang-seok Ma, Seongnam-si (KR); Joon-shik Park, Yongin-si (KR); Ji-young Oh, Suwon-si (KR); Jong-suk Chung, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 365 days.

(21) Appl. No.: 11/335,229

(22) Filed: Jan. 19, 2006

(65) Prior Publication Data

US 2006/0183142 A1    Aug. 17, 2006

(30) Foreign Application Priority Data

Jan. 22, 2005    (KR) ...................... 10-2005-0006085

(51) Int. Cl.
   C12P 19/34    (2006.01)
   C12Q 1/68     (2006.01)
   C07H 21/02    (2006.01)
   C07H 21/04    (2006.01)
   C07H 21/00    (2006.01)

(52) U.S. Cl. .................. 435/6; 435/91.1; 536/23.1; 536/24.3; 536/24.33; 536/25.3; 536/25.32

(58) Field of Classification Search ............. 435/6, 435/91.1, 183; 436/94, 501; 536/23.1, 24.3, 536/24.33, 25.3, 25.32
   See application file for complete search history.

(56) References Cited

U.S. PATENT DOCUMENTS

| 5,780,233 A | 7/1998 | Guo et al. |
| 6,200,753 B1 | 3/2001 | Nathan |
| 2003/0134291 A1 | 7/2003 | Lipshutz et al. |

FOREIGN PATENT DOCUMENTS

JP    2000511434 T    9/2000

OTHER PUBLICATIONS

Conner, Brenda J. et al., "Detection of sickle cell Bs-glovin allele by hybridization with synthetic oligonucleotides," *Proc. Natl. Acad. Sci. USA* (1983) 80: 278-282.

Guo, Zhen et al., "Enhanced discrimination of single nucleotide polymorphisms by artificial mismatch hybridization," *Nature Biotechnology* (1997) 15: 331-335.

(Continued)

*Primary Examiner*—Frank W Lu
(74) *Attorney, Agent, or Firm*—Cantor Colburn LLP (57) ABSTRACT

A method of increasing discrimination for a target DNA having a polymorphic site is provided. The method comprising immobilizing first and second probes on a substrate; hybridizing the immobilized first and second probes with first and second hurdle DNAs, respectively; and hybridizing the target DNA with the hybrids, and determining the ratio of a signal of the target DNA hybridized to the first probe to a signal of the target DNA hybridized to the second probe. The addition of a hurdle DNA and variation of a probe base can improve an ability of discriminating a single base mismatch.

7 Claims, 6 Drawing Sheets

OTHER PUBLICATIONS

Santalucia, John Jr., "A unified view of polymer, dumbbell, and oligonucleotide DNA nearest-neighbor thermodynamics," *Proc. Natl. Acad. Sci. USA* (1998) 95: 1460-1465.

Extended European Search Report for European Application No. 06000611.1-2405.

R. Bruce Wallace, et al.; "The use of synthetic oligonucleotides as hybridization probes. II. Hybridization of oligonucleotides of mixed sequence to rabbit beta-globin DNA"; Nucleic Acids Research; vol. 9, No. 4, pp. 879-894, 1981.

Tibanyenda, et al.; "The effect of single base-pair mismatches on the duplex stability of d(T-A-T-T-A-A-T-A-T-C-A-A-G-T-T-G) . d(C-A-A-C-T-T-G-A-T-A-T-T-A-A-T-A)"; Eur. J. Biochem.; vol. 139, 19-27, 1984.

Ebel, et al.; "Very Stable Mismatch Duplexes: Structural and Thermodynamic Studies on Tandem G.A Mismatches in DNA"; Biochem.; vol. 31, pp. 12083-12086, 1992.

Xia, et al.; "Thermodynamic Parameters for an Expanded Nearest-Neighbor Model for Formation of RNA Duplexes with Watson-Crick Base Pairs"; Biochem.; vol. 37, pp. 14719-14735, 1998.

JP Appln. No. 2006011737; JPO Action Date Sep. 19, 2008, Abstract only.

⇕ NATURAL MISMATCH
↑ ARTIFICIAL BASE MISMATCH

| DETECTION METHOD | NORMAL | HURDLE | HURDLE + BASE VARIATION | BASE VARIATION |
|---|---|---|---|---|
| IMAGE | PM / MM | PM / MM | PM / MM | PM / MM |
| PM/MM RATIO | 1.76 ± 0.36 | 1.53 ± 0.26 | 8.33 ± 1.28 | 4.92 ± 0.97 |

METHOD OF INCREASING DISCRIMINATION FOR SINGLE BASE MISMATCH USING HURDLE DNA AND ARTIFICIALLY MISMATCHED PROBE

CROSS-REFERENCE TO RELATED PATENT APPLICATION

This application claims the benefit of Korean Patent Application No. 10-2005-0006085, filed on Jan. 22, 2005, in the Korean Intellectual Property Office, the disclosure of which is incorporated herein in its entirety by reference.

BACKGROUND OF THE INVENTION

1. Field of the Invention

The present invention relates to a method of increasing discrimination for a single base mismatch using a hurdle DNA and an artificially mismatched probe.

2. Description of the Related Art

A standard method for detecting a variation in a nucleic acid sequence depends upon specific recognition by one oligonucleotide strand of a complementary nucleic acid target strand. When the probe and the target are not identical, the affinity of the two strands for one another is reduced. Reduced affinity is manifested by a decrease in duplex thermal stability which can be conveniently monitored by measuring the duplex melting temperature (Tm). The difference in duplex melting temperatures (ΔTm) between, on the one hand, a perfectly matched probe and target and, on the other hand, the same probe with a second target that differs from the first target at one nucleotide, has proven useful in detecting sequence variations in DNA. Wallace, B. R. et al., Nucleic Acids Research 9:879 (1981) discriminated between short oligomers differing at a single base. Subsequently, Conner, B. J. et al., Proceedings of the National Academy of Sciences USA 80:278 (1983) used the Wallace approach to investigate point mutations in the β-globin gene. As a result, duplex thermal stability can be reasonably accurately predicted on the basis of sequences between probe and target.

Although hybridization can be a useful and powerful technique, it is limited in that the stability difference between a perfectly matched duplex and a mismatched duplex, particularly if the mismatch is only a single base, can be quite small, corresponding to a difference in Tm between the two of as little as 0.5° C. See Tibanyenda, N. et al., Eur. J. Biochem. 139:19 (1984) and Ebel, S. et al., Biochem. 31:12083 (1992). More importantly, it is understood that as the length of the oligomeric probe increases, the negative effect of a single base mismatch on overall duplex stability decreases. This is an important limitation because it is desirable to increase probe length to enhance hybridization specificity for single genes while excluding weakly related genes. Thus, the ability to specifically distinguish closely related genes has not kept pace with the desire to focus hybridization studies on increasingly narrow regions of the genome. What is desired is a method that improves the ability to distinguish closely related genes by increasing the difference in melting temperatures of duplexes formed between probe and target.

U.S. Pat. No. 6,764,693 discloses a nucleic acid hybridization method of improving an ability to distinguish a control nucleic acid target and a mutant nucleic acid target including sequence variation using a modified oligonucleotide. Artificial mismatch is induced using 1-(2'-deoxy-β-D-ribofuranosyl)-3-nitropyrrole as a base analogue to increase discrimination for a single base mismatch. However, synthesis of the base analogue is difficult and there is no description regarding blocking effect due to the addition of a hurdle DNA of the present invention.

The inventors of the present invention studied a method of increasing discrimination for a single base mismatch based on conventional technologies described above and found that by using the addition of a hurdle DNA and variation of a probe base, discrimination for a single base mismatch is increased. Thus, the present invention is completed.

SUMMARY OF THE INVENTION

The present invention provides a method of increasing discrimination for a single base mismatch using a hurdle DNA and an artificially mismatched probe.

According to an aspect of the present invention, there is provided a method of increasing discrimination for a target DNA having a polymorphic site, the method including: synthesizing a first probe by artificially substituting a base of a probe which is fully complementary to a target DNA having a polymorphic site by a mismatched natural base and synthesizing a second probe by artificially substituting a base of another probe having a single base mismatch at a position corresponding to the polymorphic site of the target DNA with a mismatched natural base; synthesizing a first hurdle DNA which is fully complementary to the first probe and is shorter than the first probe and a second hurdle DNA which is fully complementary to the second probe and is shorter than the second probe; immobilizing the first and second probes on a substrate; hybridizing the immobilized first and second probes with the first and second hurdle DNAs, respectively; and hybridizing the target DNA with the hybrids.

BRIEF DESCRIPTION OF THE DRAWINGS

The above and other features and advantages of the present invention will become more apparent by describing in detail exemplary embodiments thereof with reference to the attached drawings in which:

FIG. 5 illustrates the fluorescence intensity of hybrids of a CY-3 labeled target DNA and each of four different probe sets of Table 1 (NORMAL block, wherein the First Probe is SEQ ID No. 1 and the Second Probe is SEQ ID No. 2; HURDLE block, wherein the First probe is SEQ ID No. 1; the First Hurdle is SEQ ID No. 5; the Second Probe is SEQ ID No. 2; and the Second Hurdle is SEQ ID No. 6; HURDLE+BASE VARIATION block, wherein the First Probe is SEQ ID No. 3; the First Hurdle is SEQ ID No. 5; the Second Probe is SEQ ID No. 4; and the Second Hurdle is SEQ ID No. 6; BASE VARIATION block, wherein the First Probe is SEQ ID No. 3 and the Second Probe is SEQ ID No. 4; PM means that the target DNA perfectly matched to the first probe of the NORMAL probe disclosed in Table 1, MM means that there is one base mismatch between the target DNA and the second probe in Table 1 when the target DNA is complementary to the second probe; PM/MM RATIO means a ratio of a signal of the target DNA bound to the first probe to a signal of the target DNA bound to the second probe);

FIG. 7 is a graph illustrating a PM/MM ratio of each probe set of Table 2, wherein PM means that the target DNA perfectly matched to the first probe of the NORMAL probe disclosed in Table 1, MM means that there is one base mismatch between the target DNA and the second probe in Table 1 when the target DNA is complementary to the second probe; PM/MM RATIO means a ratio of a signal of the target DNA bound to the first probe to a signal of the target DNA bound to the second probe; 1MM, 2MM, 1MM+H, and 2MM+H mean probe set in which one base was artificially mismatched, probe set in which two bases were artificially mismatched, probe set in which one base was artificially mismatched+ introduction of hurdle DNA, and probe set in which two bases was artificially mismatched+introduction of hurdle DNA, respectively.

DETAILED DESCRIPTION OF THE INVENTION

A method of increasing discrimination for a target having a polymorphic site according to an embodiment of the present invention includes: synthesizing a first probe by artificially substituting a base of a probe which is fully complementary to a target DNA having a polymorphic site by a mismatched natural base and ynthesizing a second probe by artificially substituting a base of another probe having a single base mismatch at a position corresponding to the polymorphic site of the target DNA with a mismatched natural base; synthesizing a first hurdle DNA which is fully complementary to the first probe and is shorter than the first probe and a second hurdle DNA which is fully complementary to the second probe and is shorter than the second probe; immobilizing the first and second probes on a substrate; hybridizing the immobilized first and second probes with the first and second hurdle DNAs, respectively; and hybridizing the target DNA with the hybrids. Here, the target DNA binds to the probe DNA via competition with the hurdle DNAs.

Figure 1:
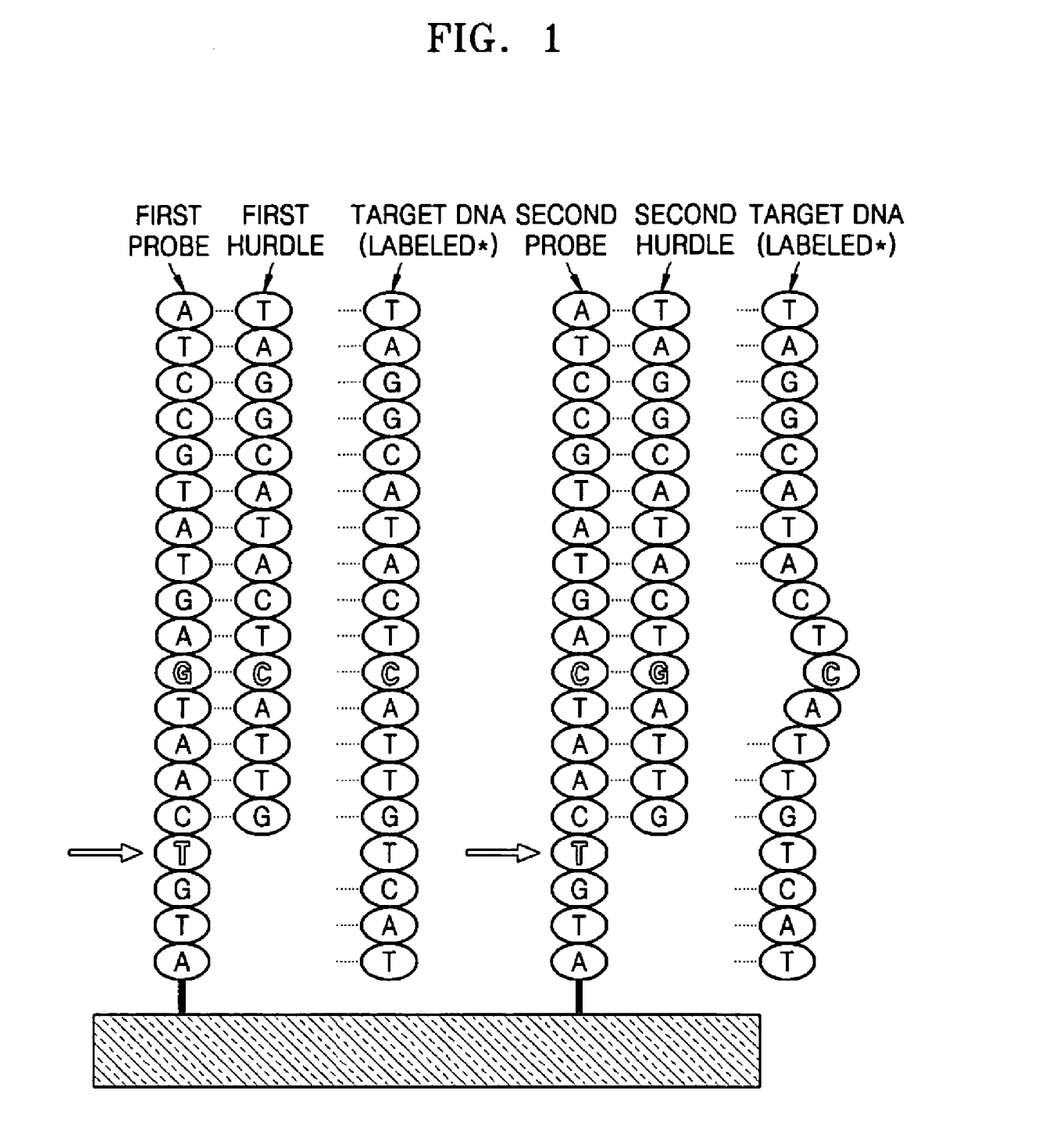
FIG. 1 schematically illustrates a method of increasing discrimination for a single base mismatch using a hurdle DNA and an artificially mismatched probe (wherein the First probe is SEQ ID No. 3; the First Hurdle is SEQ ID No. 5; the Target DNA is SEQ ID No. 7; the Second Probe is SEQ ID No. 4; and the Second Hurdle is SEQ ID No. 6)

In the method of the present embodiment, a hurdle DNA and a probe having a modified base are used to increase discrimination for a single base mismatch in a DNA chip. FIG. 1 schematically illustrates a method of increasing discrimination for a single base mismatch using a hurdle DNA and an artificially mismatched probe according to an embodiment of the present invention. Referring to FIG. 1, a first probe and a target DNA are complementary to each other in all portions other than one artificially mismatched base (T-T, indicated by an arrow) and a second probe includes a mismatched base (C-C) on a target DNA and an artificially mismatched base (T-T, indicated by an arrow). A first hurdle DNA is fully complementary to the first probe and is shorter than the first probe. A second hurdle DNA is fully complementary to the second probe and is shorter than the second probe. The first hurdle DNA has the same sequence length as the second hurdle DNA.

For purposes of this patent application, a "target DNA" can be a chromosome or any portion thereof, or can be a recombinant nucleic acid molecule such as a plasmid, oligonucleotide, or other nucleic acid fragment, and may be naturally occurring or synthetic. When the target is DNA, it is understood that the DNA is provided for use in the method in a denatured or single-stranded form capable of hybridizing to a single-stranded oligonucleotide probe.

Figure 4:
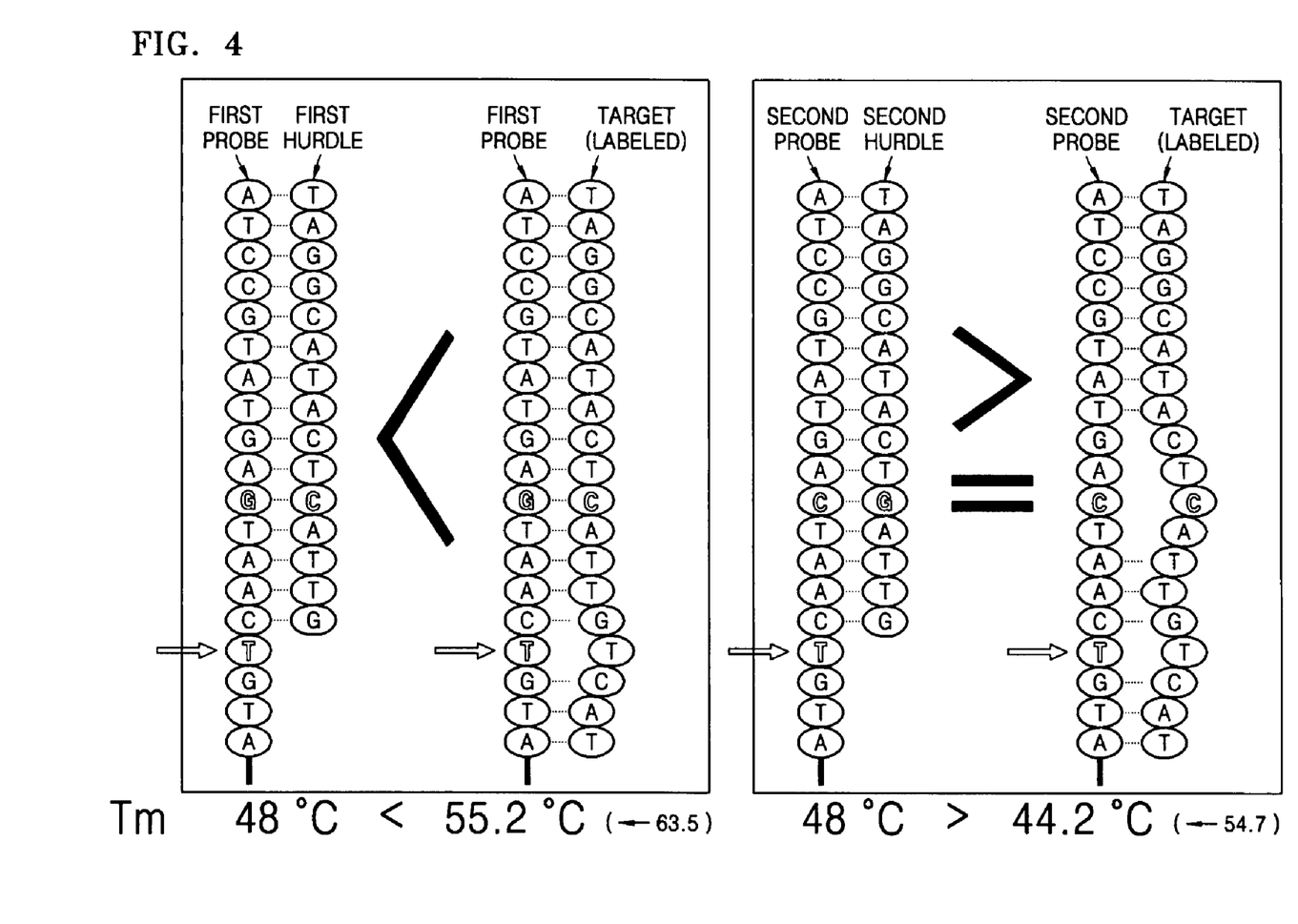
FIG. 4 illustrates Tm of hybrids of artificially mismatched probes and hurdle DNAs and Tm of hybrids of the artificially mismatched probes and a target DNA (wherein the First Probe is SEQ ID No. 3; the First Hurdle is SEQ ID No. 5; the Target DNA is SEQ ID No. 7; the Second Probe is SEQ ID No. 4; and the Second Hurdle is SEQ ID No. 6)

In a conventional method, an artificially mismatched base is introduced into a probe to distinguish a single base mismatch without using the first hurdle DNA and the second hurdle DNA. However, in the method of the present embodiment, the hurdle DNA is hybridized with the probe before hybridizing the target DNA with the probe. Since the first hurdle DNA is shorter than the target DNA, the melting point (Tm) of the hybrid of the first hurdle DNA and the first probe is lower than that of the hybrid of the target DNA and the first probe. Thus, under suitable hybridization conditions, substitution of the first hurdle DNA previously hybridized with the first probe by the target DNA occurs. Meanwhile, even though the second hurdle DNA is shorter than the target DNA, the melting point (Tm) of the hybrid of the second hurdle DNA and the second probe is higher than that of the hybrid of the target DNA and the second probe (FIG. 4). This is because the second probe includes one mismatched base. Thus, under suitable hybridization conditions, substitution of the second hurdle DNA previously hybridized with the second probe by the target DNA does not occur. Consequently, the second hurdle DNA prevents a non-complementary target DNA from hybridizing to the second probe.

That is, while the first hurdle DNA is easily substituted by the target DNA, the second hurdle DNA is not easily substituted by the target DNA. Therefore, the target DNA more easily hybridizes to the first probe than to the second probe. Thus, an ability to discriminate a single base mismatch can be improved. This can be more easily observed when a fluorescence labeled target DNA is used in the experiment and a difference in relative intensity of fluorescence, i.e., a ratio of a fluorescence intensity of the target DNA hybridized to the first probe with respect to a fluorescence intensity of the target DNA hybridized to the second probe. As a difference in the fluorescence intensity increases, the ability to discriminate a single base mismatch increases.

Also, the mismatched base can be located at a position corresponding to a polymorphic site of the target. Single nucleotide polymorphism (SNP) refers to one or tens of base variations among 3 billion base sequences of a chromosome in a cell nucleus from different individuals. An exemplary disease resulting from the SNP is sickle cell anemia, which is caused due to substitution of a single base at a specific site by another base. To discriminate one mismatch occurring at a specific site of a gene, the method of the present embodiment is required.

Figure 2:
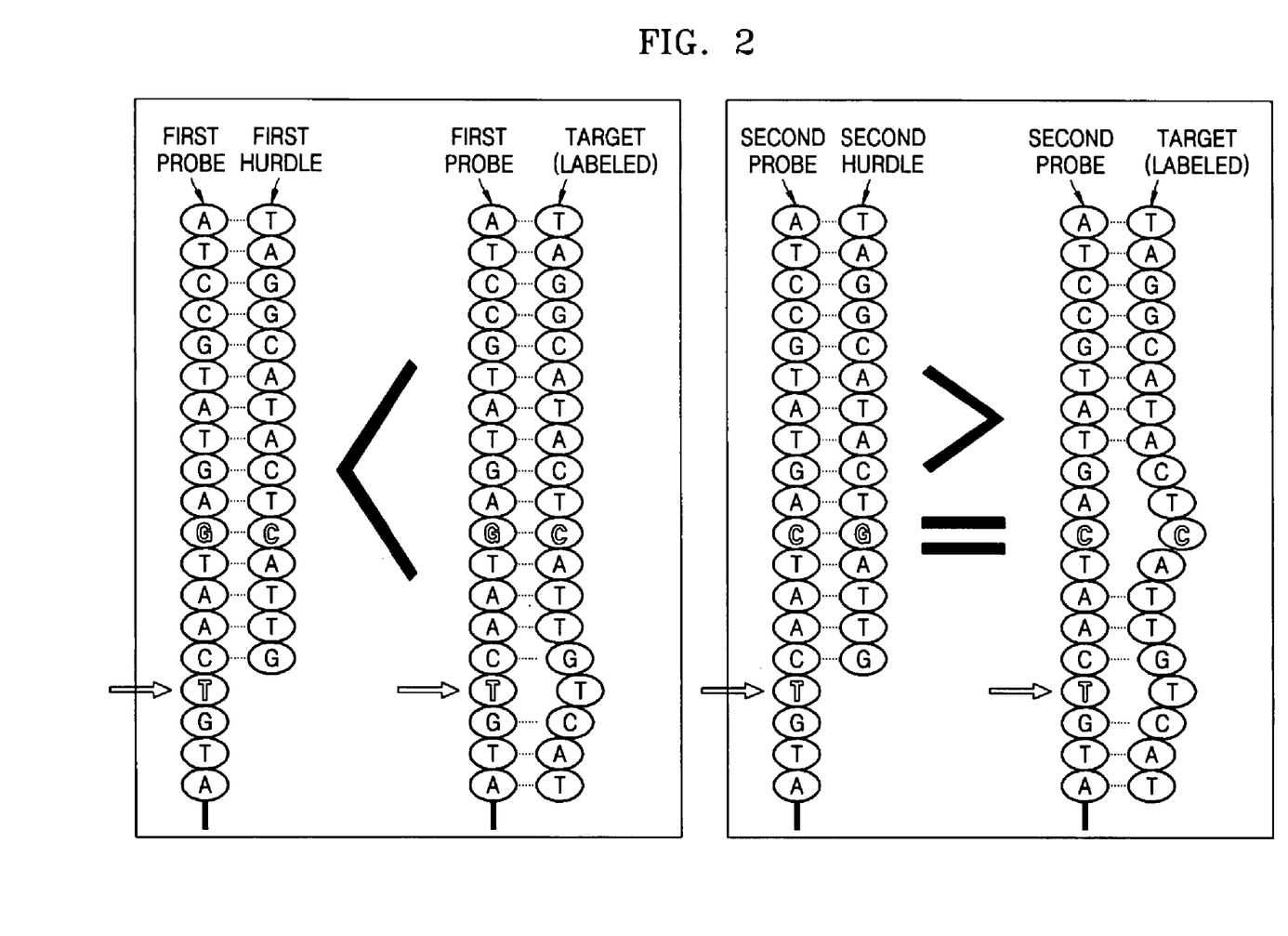
FIG. 2 schematically illustrates the relative stability of a hybrid of an artificially mismatched probe and a hurdle DNA and a hybrid of the artificially mismatched probe and a target DNA (wherein the First Probe is SEQ ID No. 3; the First Hurdle is SEQ ID No. 5; the Target DNA is SEQ ID No. 7; the Second Probe is SEQ ID No. 4; and the Second Hurdle is SEQ ID No. 6)

In an embodiment of the present invention, the first probe and the second probe may further include an artificially mismatched base at the same position. FIG. 2 schematically illustrates the relative stability of a hybrid of a probe DNA and a hurdle DNA and a hybrid of the probe DNA and a target DNA, the probe DNA having an artificially mismatched base for increasing discrimination for a single base mismatch. In the method of the present invention, when only a hurdle DNA is used to discriminate a single base mismatch, a difference in the melting temperature between the hybrid of the first probe and the target DNA and the hybrid of the second probe and the target DNA is relatively small, and thus efficient discrimination for a single base mismatch cannot be achieved. Thus, to more efficiently discriminate a single base mismatch, an artificially mismatched base is introduced into a probe (in FIGS. 2 and 4, A in an original probe sequence is substituted by T at a position indicated by an arrow). That is, when an artificially mismatched base is introduced into the first probe and the second probe at the same position, an ability to discriminate a single base mismatch is improved as demonstrated in the following Examples.

In an embodiment of the present invention, the polymorphic site may be produced by one selected from the group consisting of substitution, addition and deletion of a nucleotide. Although a mismatch resulting from substitution of a nucleic acid for the target DNA is described above, addition and deletion of a nucleic acid are also included.

In an embodiment of the present invention, the artificial mismatch may be produced in two nucleotides. Even though one artificially mismatched base can be introduced into a probe, two or more artificially mismatched bases can also be introduced to increase discrimination for a single base mismatch. This can be appropriately applied according to a target DNA. Preferably, the artificial mismatch is produced in two nucleotides.

In an embodiment of the present invention, the artificial mismatches may be continuously arranged or be separated by one or more nucleotides. When two or more artificial mismatches are produced, an artificially mismatched base may be introduced into a nucleotide and another artificially mismatched base may be introduced into a nucleotide adjacent to the mismatched nucleotide. Alternatively, an artificially mismatched base may be introduced into a nucleotide and another artificially mismatched base may be introduced into a nucleotide separated from the mismatched nucleotide by one or more nucleotides. This can be appropriately applied according to a target DNA. When the artificial mismatches are separated by one or more nucleotides, they are preferably separated by 8-20 nucleotides.

In an embodiment of the present invention, the polymorphic site and the artificial mismatch may be separated by one or more nucleotides. A mismatch present in a region in which hybridization of the hurdle DNA occurs and an artificial mismatch may be separated by one or more nucleotides, preferably by 3-15 nucleotides.

The present invention will now be described in greater detail with reference to the following examples. The following examples are for illustrative purposes only and are not intended to limit the scope of the invention.

EXAMPLE 1

Discrimination for Single Base-Substituted DNA

To investigate the effect of discriminating a single base-substituted DNA, the following 4 different probe sets were used.

TABLE 1

```
[1] (Normal probe set)
First    Surface
probe    5'-ATGACAATGAGTATGCCTA-3'    (SEQ ID No: 1)

Second   Surface
probe    5'-ATGACAATCAGTATGCCTA-3'    (SEQ ID No: 2)

[2] (Probe set in which one base was artificially
mismatched)
First    Surface
probe    5'-ATGTCAATGAGTATGCCTA-3'    (SEQ ID No: 3)

Second   Surface
probe    5'-ATGTCAATCAGTATGCCTA-3'    (SEQ ID No: 4)

[3] (Normal probe set + introduction of hurdle
DNA)
First    Surface
probe    5'-ATGACAATGAGTATGCCTA-3'    (SEQ ID No: 1)

3'-GTTACTCATACGGAT-5'         (SEQ ID No: 5)
         (hurdle DNA)

Second   Surface
probe    5'-ATGACAATCAGTATGCCTA-3'    (SEQ ID No: 2)

3'-GTTACTCATACGGAT-5'         (SEQ ID No: 6)
         (hurdle DNA)

[4] (Probe set in which one base was artificially
mismatched + Introduction of hurdle DNA)
First    Surface
probe    5'-ATGTCAATGAGTATGCCTA-3'    (SEQ ID No: 3)

3'-GTTACTCATACGGAT-5'         (SEQ ID No: 5)
         (hurdle DNA)

Second   Surface
probe    5'-ATGTCAATCAGTATGCCTA-3'    (SEQ ID No: 4)

3'-GTTACTCATACGGAT-5'         (SEQ ID No: 6)
         (hurdle DNA)
```

4 different DNA probe sets represented in Table 1 were immobilized on an amino-silane coated wafer using a conventional immobilization technique in a concentration of 1 µM. Hybridization of a hurdle DNA to a probe DNA was performed by reacting a 1 µM hurdle DNA with the DNA probe at 40° C. for 1 hour.

The prepared 4 different DNA probe sets were hybridized with a 2 nM CY-3 labeled target oligomer (5'-TAGGCATACTCATTGTCAT-3') (SEQ ID No: 7, perfectly matched to the first probe of the normal probe set disclosed in Table 1 and mismatched to the second probe in one base) at 40° C. for 1 hour. Thereafter, the chip was washed with a 3×SSC solution for 5 minutes under gentle stirring, and then further washed with 1×SSC solution for 5 minutes. After the chip was dried, the fluorescence intensity was measured using a scanner (CY-3) at 532 nm to determine a ratio of a signal of the target DNA bound to the first probe to a signal of the target DNA bound to the second probe [PM (perfectly matched)/MM (mismatched)]. The Tm values were calculated using Santalucia parameter (1998).

Figure 3:
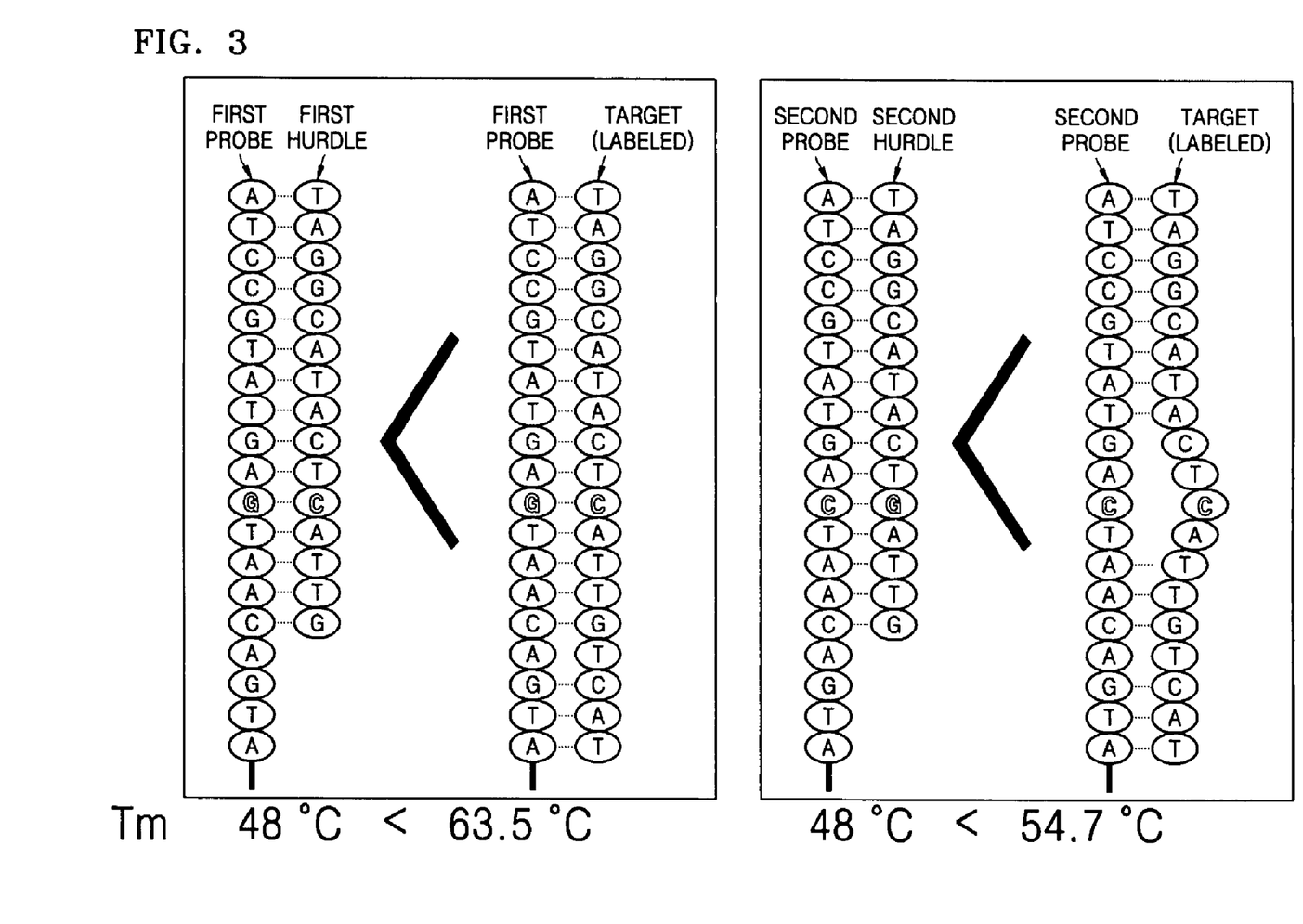
FIG. 3 schematically illustrates relative stability of a hybrid of a normal probe and a hurdle DNA and a hybrid of the normal probe and a target DNA (wherein the First probe is SEQ ID No. 1; the First Hurdle is SEQ ID No. 5; the Target DNA is SEQ ID No. 7; the Second Probe is SEQ ID No. 2; and the Second Hurdle is SEQ ID No. 6)

FIG. 3 illustrates the relative stability of a hybrid of a normal probe DNA and a hurdle DNA and a hybrid of a normal probe DNA and a target DNA. Referring to FIG. 3, as a result of calculating Tm using probe set No. 3 Tm of the hybrid of the first probe and the target DNA was higher than Tm of the hybrid of the first probe and the first hurdle DNA, and thus the hybrid of the first probe and the target DNA was more stable. Thus, the first hurdle DNA could be easily substituted by the target DNA. Also, the hybrid of the second probe and the target DNA had Tm higher than the hybrid of the second probe and the second hurdle DNA, and thus the hybrid of the second probe and the target DNA was more stable. Thus, the second hurdle DNA could be easily substituted by the target DNA. This is the result contrary to the object of the present invention requiring that the first hurdle DNA should be easily substituted by the target DNA and the second hurdle DNA shouldn't be easily substituted by the target DNA. However, this is the result obtained from an example of the present invention.

Thus, to improve an ability to discriminate a single base mismatch, one base variation was introduced into the first probe and the second probe at the same position. FIG. 4 illustrates Tm of a hybrid of an artificially mismatched probe and a hurdle DNA and Tm of a hybrid of an artificially mismatched probe and a target DNA. Referring to FIG. 4, one base variation (A→T) was introduced at the site indicated by an arrow and Tm values were calculated. As a result, Tm of the hybrid of the first probe and the first hurdle DNA was unchanged and Tm of the hybrid of the first probe and the target DNA was reduced from 63.5° C. to 55.2° C. However, the hybrid of the first probe and the target DNA still had Tm higher than the hybrid of the first probe and the first hurdle DNA, and thus were more stable. Therefore, the first hurdle DNA can be easily substituted by the target DNA. Meanwhile, Tm of the hybrid of the second probe and the second hurdle DNA was unchanged and Tm of the hybrid of the second probe and the target DNA was reduced from 54.7° C. to 44.2° C. However, the hybrid of the second probe and the target DNA had Tm lower than the hybrid of the second probe and the second hurdle DNA, and thus were more unstable. Therefore, the second hurdle DNA cannot be easily substituted by the target DNA. This is the result coinciding with the object of the present invention requiring that the first hurdle DNA should be easily substituted and the second hurdle DNA should not be easily substituted. Also, this result match with the PM/MM ratio obtained after hybridizing the target DNA with probes (see FIG. 5).

Figure 5:
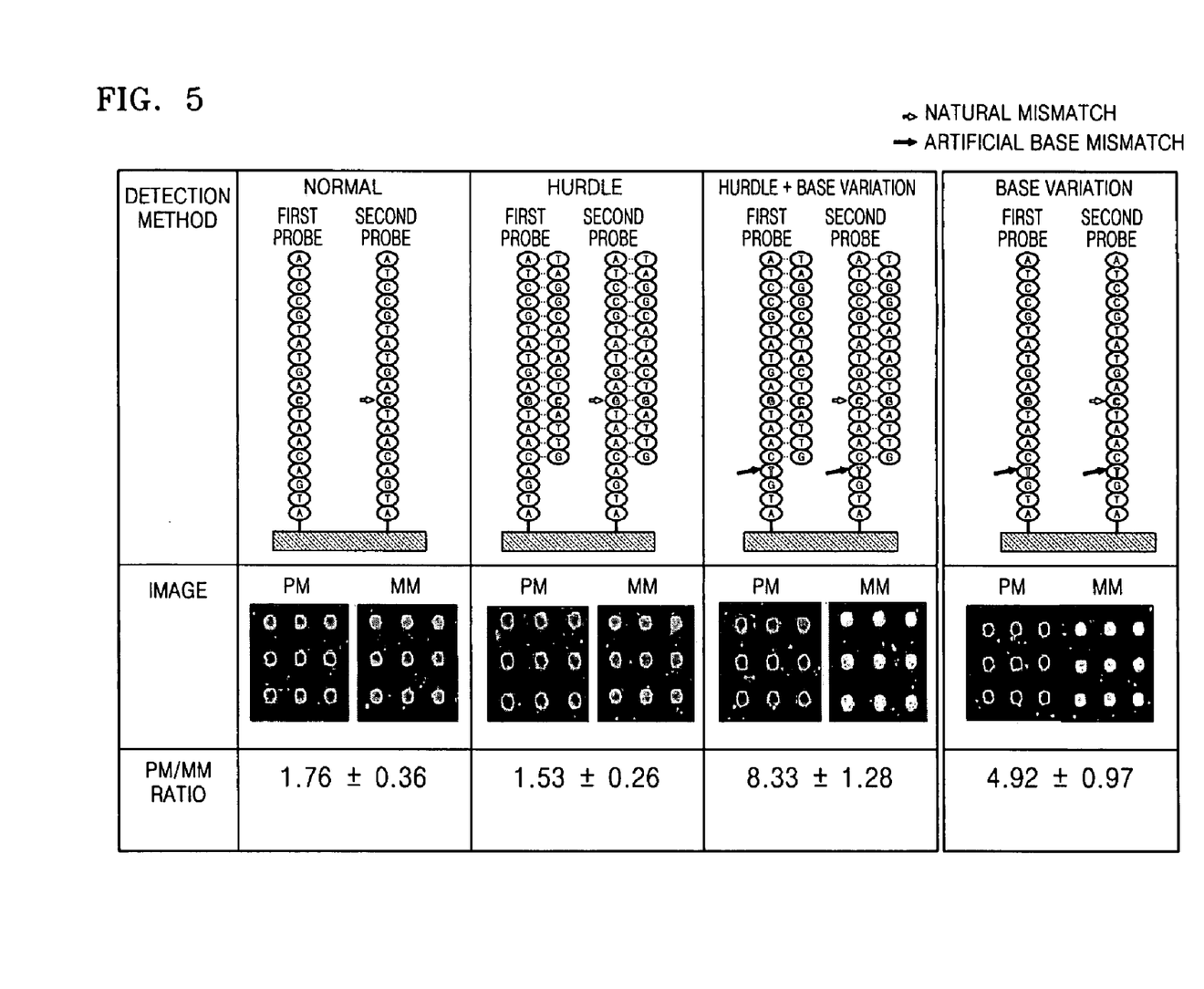
Figure 6:
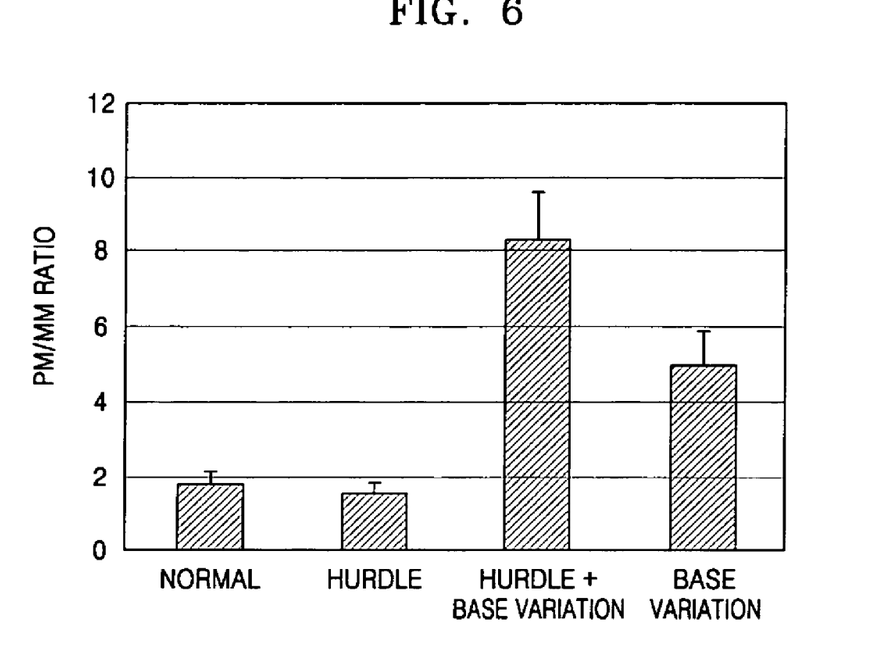
FIG. 6 is a graph illustrating a PM (perfectly matched)/MM (mismatched) ratio of each probe set of Table 1, wherein PM means that the target DNA perfectly matched to the first probe of the NORMAL probe disclosed in Table 1, MM means that there is one base mismatch between the target DNA and the second probe in Table 1 when the target DNA is complementary to the second probe; PM/MM RATIO means a ratio of a signal of the target DNA bound to the first probe to a signal of the target DNA bound to the second probe)

FIG. 5 illustrates the fluorescence intensity measured after hybridizing the CY-3 labeled target DNA with 4 different probe sets. FIG. 6 is a graph illustrating the PM/MM ratio of each probe (normal=probe set #1, hurdle=probe set #3, hurdle+base variation=probe set #4, base variation=probe set #2). Referring to FIGS. 5 and 6, the introduction of the hurdle DNA and a base variation significantly increased the PM/MM ratio compared to the normal probe set. Also, the introduction of only a base variation increased the PM/MM ratio compared to the normal probe set. However, the introduction of only a hurdle DNA showed the PM/MM ratio nearly identical to the normal probe set. However, the results can vary depending on the sequence and the length of a probe and the length of a hurdle DNA. That is, when the sequence and the length of a probe and the length of a hurdle DNA are appropriately selected, the effect of the present invention can be obtained even by the introduction of only a hurdle DNA.

EXAMPLE 2

Discrimination for Single Base-Inserted DNA

To investigate discrimination for a single base-inserted DNA, 5 different probe sets as presented in Table 2 were used.

TABLE 2

```
[1] (Normal probe set)
First  Surface
probe  5'-cccccTCCCCCCTgtcagca-3'   (SEQ ID No: 8)

Second Surface
probe  5'-cccccTCCCCCCTgtcagca-3'   (SEQ ID No: 9)

[2] (Probe set in which one base was artificially
mismatched)
First  Surface
probe  5'-cctccTCCCCCCTgtcagca-3'   (SEQ ID No: 10)

Second Surface
probe  5'-cctccTCCCCCCTgtcagca-3'   (SEQ ID No: 11)

[3] (Probe set in which two bases were
artificially mismatched)
First  Surface
probe  5'-cctccTCCCCCCTgtcaaca-3'   (SEQ ID No: 12)

Second Surface
probe  5'-cctccTCCCCCCTgtcaaca-3'   (SEQ ID No: 13)

[4] (Probe set in which one base was artificially
mismatched + Introduction of hurdle DNA)
First  Surface
probe  5'-cctccTCCCCCCTgtcagca-3'   (SEQ ID No: 10)

3'-gaggAGGGGGGAcagtcgt-5'    (SEQ ID No: 14)
       (hurdle DNA)

Second Surface
probe  5'-cctccTCCCCCCTgtcagca-3'   (SEQ ID No: 11)

3'-gaggAGGGGGGAcagtcgt-5'    (SEQ ID No: 15)
       (hurdle DNA)

[5] (Probe set in which two bases were
artificially mismatched + Introduction of hurdle
DNA)
First  Surface
probe  5'-cctccTCCCCCCTgtcaaca-3'   (SEQ ID No: 12)

3'-gaggAGGGGGGAcagttgt-5'    (SEQ ID No: 16)
       (hurdle DNA)

Second Surface
probe  5'-cctccTCCCCCCTgtcaaca-3'   (SEQ ID No: 13)

3'-gaggAGGGGGGAcagttgt-5'    (SEQ ID No: 17)
       (hurdle DNA)
```

The experimental procedure was the same as described in Example 1 and the target DNA sequence was 5'-tgctgacAGGGGGGAggggg-3' (SEQ ID No: 18).

Figure 7:
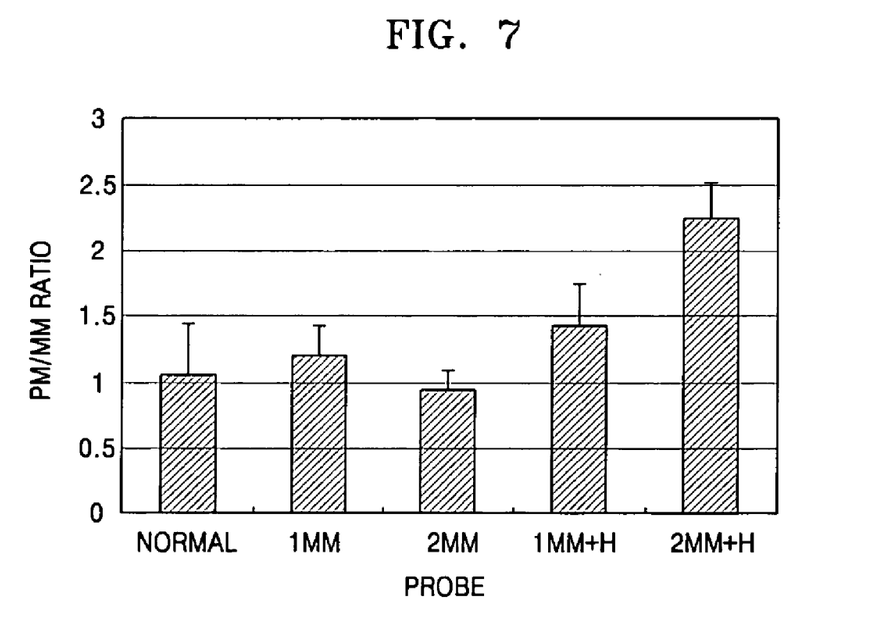

FIG. 7 is a graph illustrating the PM/MM ratio of each probe set of Table 2 (normal=probe set #1, 1 MM=probe set #2, 2 MM=probe set #3, 1 MM+H=probe set #4, 2 MM+H=probe set #5). Referring to Table 7, it is apparent that the introduction of the hurdle DNA and two base mismatches significantly increased the PM/MM ratio compared to the normal probe set. Also, it can be seen that the introduction of the hurdle DNA and one base mismatch increased the PM/MM ratio compared to the normal probe set.

As described above, the addition of a hurdle DNA and variation of a probe base can improve an ability of discriminating a single base mismatch.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting a polymorphism site in a target DNA having the polymorphic site, the method comprising:

synthesizing a first probe by artificially substituting a base of a probe which is fully complementary to the test target DNA with a mismatched natural base such that the base on the polymorphic site of the test target DNA is fully complementary to its corresponding base in the first probe and the mismatched natural base in the first probe is not complementary to its corresponding base in the test target DNA;

synthesizing a second probe by artificially substituting a base of another probe having a single base mismatch at the position corresponding to the polymorphic site of the target DNA with a mismatched natural base such that the base on the polymorphic site of the test target DNA is not complementary to its corresponding base in the second probe and the mismatched natural base in the second probe is not complementary to its corresponding base in the test target DNA, wherein the base of the another probe substituted by the mismatched natural base is not at the position corresponding to the polymorphic site of the target DNA;

synthesizing a first hurdle DNA which is fully complementary to the first probe and is shorter than the first probe, wherein the melting temperature (Tm) of the hybrid of the first hurdle DNA and the first probe is lower than that of the hybrid of the target DNA and the first probe;

synthesizing a second hurdle DNA which is fully complementary to the second probe and is shorter than the second probe, wherein the melting temperature (Tm) of the hybrid of the second hurdle DNA and the second probe is higher than that of the hybrid of the target DNA and the second probe;

immobilizing the first and second probes on a substrate and forming immobilized first and second probes;

hybridizing the immobilized first and second probes with the first and second hurdle DNAs, respectively;

hybridizing the test target DNA with the immobilized first and second probes following the hybridizing the immobilized first and second probes with the first and second hurdle DNAs under conditions such that the first hurdle DNA is easily substituted by the target DNA and the second hurdle DNA is not easily substituted by the target DNA;

determining the ratio of the relative amount of the test target DNA hybridized to the first probe to the relative amount of the test target DNA hybridized to the second probe thereby detecting the polymorphic site of the test target DNA based on the ratio of the relative amount of the test target DNA hybridized to the first probe to the relative amount of the test target DNA hybridized to the second probe.

2. The method of claim 1, wherein the first and second probe have the same length, and the mismatched natural bases in the first probe and the second probe occur at the same position.

3. The method of claim 1, wherein the polymorphic site of the target DNA is produced by substitution of a nucleotide of a parent DNA of the target DNA or addition of a nucleotide into the parent DNA of the target DNA or deletion of a nucleotide of the parent DNA of the target DNA.

4. The method of claim 2, further comprising introducing two or more mismatched bases into the first probe or the second probe.

5. The method of claim 4, wherein the mismatched bases are continuously arranged or are separated by one or more nucleotides.

6. The method of claim 5, wherein the mismatched bases are separated by 8-20 nucleotides.

7. The method of claim 1, wherein the test target DNA is a fluorescently labeled test target DNA, and the ratio of the relative amount of the test target DNA hybridized to the first probe to the relative amount of the test target DNA hybridized to the second probe is determined by measuring the ratio of the fluorescence intensity of the fluorescently labeled test target DNA hybridized to the first probe to the fluorescence intensity of the fluorescently labeled test target DNA hybridized to the second probe.

* * * * *

SEQUENCE LISTING

<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: probe DNA

<400> SEQUENCE: 1
atgacaatga gtatgccta                                              19

<210> SEQ ID NO 2
<211> LENGTH: 19
<212> TYPE: DNA
<213> ORGANISM: Artificial Sequence
<220> FEATURE:
<223> OTHER INFORMATION: probe DNA

<400> SEQUENCE: 2
atgacaatca gtatgccta                                              19

<210> SEQ ID NO 3
<211> LENGTH: 19
<212> TYPE: DNA
<213> ORGANISM: Artificial Sequence
<220> FEATURE:
<223> OTHER INFORMATION: probe DNA

<400> SEQUENCE: 3
atgtcaatga gtatgccta                                              19

<210> SEQ ID NO 4
<211> LENGTH: 19
<212> TYPE: DNA
<213> ORGANISM: Artificial Sequence
<220> FEATURE:
<223> OTHER INFORMATION: probe DNA

<400> SEQUENCE: 4
atgtcaatca gtatgccta                                              19

<210> SEQ ID NO 5
<211> LENGTH: 15
<212> TYPE: DNA
<213> ORGANISM: Artificial Sequence
<220> FEATURE:
<223> OTHER INFORMATION: hurdle DNA

<400> SEQUENCE: 5
taggcatact cattg                                                  15

<210> SEQ ID NO 6
<211> LENGTH: 15
<212> TYPE: DNA
<213> ORGANISM: Artificial Sequence
<220> FEATURE:
<223> OTHER INFORMATION: hurdle DNA

<400> SEQUENCE: 6
taggcatact gattg                                                  15

<210> SEQ ID NO 7
<211> LENGTH: 19

```
<212> TYPE: DNA
<213> ORGANISM: Artificial Sequence
<220> FEATURE:
<223> OTHER INFORMATION: target DNA

<400> SEQUENCE: 7
taggcatact cattgtcat                                              19

<210> SEQ ID NO 8
<211> LENGTH: 20
<212> TYPE: DNA
<213> ORGANISM: Artificial Sequence
<220> FEATURE:
<223> OTHER INFORMATION: probe DNA

<400> SEQUENCE: 8 cccccctcccc cctgtcagca                                            20

<210> SEQ ID NO 9
<211> LENGTH: 21
<212> TYPE: DNA
<213> ORGANISM: Artificial Sequence
<220> FEATURE:
<223> OTHER INFORMATION: probe DNA

<400> SEQUENCE: 9 cccccctcccc ccctgtcagc a                                          21

<210> SEQ ID NO 10
<211> LENGTH: 20
<212> TYPE: DNA
<213> ORGANISM: Artificial Sequence
<220> FEATURE:
<223> OTHER INFORMATION: probe DNA

<400> SEQUENCE: 10
cctcctcccc cctgtcagca                                             20

<210> SEQ ID NO 11
<211> LENGTH: 21
<212> TYPE: DNA
<213> ORGANISM: Artificial Sequence
<220> FEATURE:
<223> OTHER INFORMATION: probe DNA

<400> SEQUENCE: 11
cctcctcccc ccctgtcagc a                                           21

<210> SEQ ID NO 12
<211> LENGTH: 20
<212> TYPE: DNA
<213> ORGANISM: Artificial Sequence
<220> FEATURE:
<223> OTHER INFORMATION: probe DNA

<400> SEQUENCE: 12
cctcctcccc cctgtcaaca                                             20

<210> SEQ ID NO 13
<211> LENGTH: 21
<212> TYPE: DNA
<213> ORGANISM: Artificial Sequence
<220> FEATURE:
<223> OTHER INFORMATION: probe DNA

<400> SEQUENCE: 13
```

-continued cctcctcccc ccctgtcaac a         21

<210> SEQ ID NO 14
<211> LENGTH: 19
<212> TYPE: DNA
<213> ORGANISM: Artificial Sequence
<220> FEATURE:
<223> OTHER INFORMATION: hurdle DNA

<400> SEQUENCE: 14
tgctgacagg ggggaggag         19

<210> SEQ ID NO 15
<211> LENGTH: 20
<212> TYPE: DNA
<213> ORGANISM: Artificial Sequence
<220> FEATURE:
<223> OTHER INFORMATION: hurdle DNA

<400> SEQUENCE: 15
tgctgacagg gggggaggag         20

<210> SEQ ID NO 16
<211> LENGTH: 19
<212> TYPE: DNA
<213> ORGANISM: Artificial Sequence
<220> FEATURE:
<223> OTHER INFORMATION: hurdle DNA

<400> SEQUENCE: 16
tgttgacagg ggggaggag         19

<210> SEQ ID NO 17
<211> LENGTH: 20
<212> TYPE: DNA
<213> ORGANISM: Artificial Sequence
<220> FEATURE:
<223> OTHER INFORMATION: hurdle DNA

<400> SEQUENCE: 17
tgttgacagg gggggaggag         20

<210> SEQ ID NO 18
<211> LENGTH: 20
<212> TYPE: DNA
<213> ORGANISM: Artificial Sequence
<220> FEATURE:
<223> OTHER INFORMATION: target DNA

<400> SEQUENCE: 18
tgctgacagg ggggaggggg         20